United States Patent [19]

Inoue et al.

[11] Patent Number: 5,380,934

[45] Date of Patent: Jan. 10, 1995

[54] PROCESS FOR PRODUCING ALANYLGUTAMINE

[75] Inventors: Kunimi Inoue; Yoshiyuki Yamada; Kazumi Amatsu, all of Sakai; Yukiteru Mimura, Shizuoka; Yasunori Nakaguchi; Hiroyuki Shinmura, both of Sakai; Yasuyuki Ono, Isehara; Yutaka Osawa, Ichikawa; Shoichi Mizutaki, Kawachinagano; Masaji Kasai, Fujisawa; Shinji Tomioka, Hashimoto, all of Japan

[73] Assignee: Kyowa Hakko Kogyo Co., Ltd., Tokyo, Japan

[21] Appl. No.: 141,622

[22] Filed: Oct. 27, 1993

[30] Foreign Application Priority Data

Oct. 29, 1992 [JP] Japan .................. 4-291139

[51] Int. Cl.$^6$ ........................... C07C 229/00
[52] U.S. Cl. ...................... 562/561; 558/50
[58] Field of Search .......................... 562/561

[56] References Cited

FOREIGN PATENT DOCUMENTS 0311057 4/1989 European Pat. Off. .
3206784 9/1983 Germany .
63-051399 3/1988 Japan .................. 562/561

OTHER PUBLICATIONS

Greenstein, "Chemistry of the Amino Acids", vol. 1, pp. 700–703 & 712–714; and vol. 2, pp. 808–816 & 1272–1295 (1961).
March, "Advanced Organic Chemistry: Reactions, Mechanisms, and Sturcutre", 4th Ed., pp. 411–413 (1992).
Y Ogata, et al., Bull. Chem. Soc. Jpn., vol. 54, No. 11 (1981) 3605–06.
Chemical Abstracts, vol. 99, No. 1 (1983) 6016a.
Shimonishi et al., Bull. Chem. Soc. J., vol. 35 (1962) 1966–70.
Shimonishi et al., Bull. Chem. Soc. J., vol. 37 (1964) 200–3.
Akibori et al., Bull. Chem. Soc. J., vol. 34 (1961) 739.
Thierfelder et al., Hoppe-Seyler's Z. Phys. Chem., vol. 105 (1919) 58–82.

Primary Examiner—Michael L. Shippen
Attorney, Agent, or Firm—Fitzpatrick, Cella, Harper & Scinto

[57] ABSTRACT

Disclosed is a process for producing alanylglutamine, which comprises reacting an N-(2-substituted)-propionylglutamine compound represented by the formula (I):

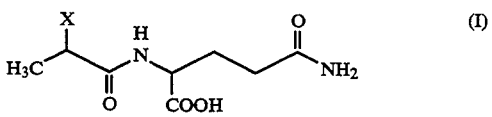

where X represents halogen, alkylsulfonyloxy, or substituted or unsubstituted arylsulfonyloxy, with ammonia at a temperature of 60° C. or below.

In accordance with the present invention, highly purified alanylglutamine can be produced in a high yield, without racemization.

2 Claims, No Drawings

PROCESS FOR PRODUCING ALANYLGUTAMINE

BACKGROUND OF THE INVENTION

The present invention relates to a process for producing alanylglutamine and a novel N-(2substituted)propionylglutamine compound which is an intermediate for the alanylglutamine. Further, the present invention relates to a process for producing the N-(2substituted)-propionylglutamine and N-(2-D-bromo)propionyl-L-glutamine, which is a known intermediate for the L-alanyl-L-glutamine. L-alanyl-L-glutamine has higher stability and higher water-solubility than L-glutamine, and is used as the component of the infusion solution.

For the production of alanylglutamine, there have heretofore been known three types of methods (1), (2) and (3): (1) methods of using a protecting group, for example, the method which comprising condensing an N-benzyloxycarbonylalanine (hereinafter referred to as a "Z-alanine") with a protected glutamine in the presence of dicyclohexylcarbodiimide (DCC), and removing the protecting group from the intermediate compound [Bull. Chem. Soc. Jpn., 34, 739 (1961); Bull. Chem. Soc. Jpn., 35, 1966 (1962)]; the method which comprising condensing a Z-alanine with a protected γ-methyl glutamate in the presence of DCC, removing the protecting group from the intermediate compound and further reacting the deprotected product with ammonia [Bull. Chem. Soc. Jpn., 37, 200 (1964)]; and the method which reacting an active ester of a Z-alanine with a non-protected glutamine and removing the protecting group from the intermediate compound (European Patent No. 311,057); (2) the method for producing alanylglutamine via an N-carboxyl anhydride (German Patent No. 3,206,784); and (3) the method using 2-bromopropionyl chloride as a starting compound via an intermediate compound, 2-bromopropionylglutamine (Hoppe-Seyler's Z. Physiol. Chem., 105, 58 (1919)).

The methods (1) using a protecting group need the step of removing the protecting group from the intermediate compound and the operation for the step is complicated. Therefore, the methods (1) yield alanylglutamine at higher cost. The method (2) uses an N-carboxyl anhydride of alanine without involving a protecting group. However, by-products such as tripeptides are considerably produced and the yield of the intended product is lower. In addition, it is difficult to purify the intended product. In the method (3), since an acid chloride having a high reactivity with water is added to an aqueous solution of glutamine for the reaction of 2-bromopropionyl chloride with glutamine, the method involves hydrolysis of the acid chloride. Therefore, the method (3) yields by-products and the yield of the intended product is low. Since the produced 2-bromopropionylglutamine is purified by extraction with an organic solvent, the yield and optical purity of the product are low. In addition, in the method (3), since the ammonolysis of 2-bromopropionylglutamine is carried out at a higher temperature, by-products are considerably produced and the optical purity of the produced alanylglutamine is often low.

SUMMARY OF THE INVENTION

An object to the present invention is to provide a process for producing alanylglutamine and a novel N-(2-substituted)propionylglutamine compound. Another object of the present invention is to provide a process for producing the N-(2-substituted)propionylglutamine and N-(2-D-bromo)propionyl-L-glutamine.

In accordance with the present invention, there is provided a process for producing alanylglutamine which comprising reacting an N-(2-substituted)propionylglutamine compound represented by the formula (I) [hereinafter referred to as Compound (I); compounds having other formulae numbers are similarly referred to]:

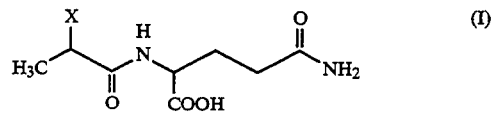

where X represents halogen, alkylsulfonyloxy, or substituted or unsubstituted arylsulfonyloxy, with ammonia at a temperature of 60° C. or below.

Further, in accordance with the present invention, there is provided a novel N-(2-substituted)propionylglutamine compound represented by the formula (I'):

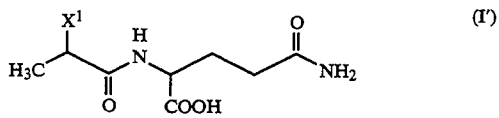

where $X^1$ represents chlorine, iodine, alkylsulfonyloxy, or substituted or unsubstituted arylsulfonyloxy, or a salt thereof.

Furthermore, in accordance with the present invention, there is provided a process for producing an N-(2-substituted)propionylglutamine compound represented by the formula (I):

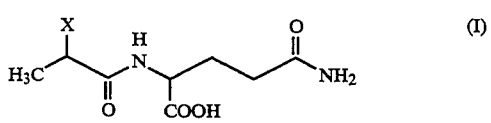

where X represents halogen, alkylsulfonyloxy, or substituted or unsubstituted arylsulfonyloxy, which comprises reacting a 2-substituted-propionyl halide represented by the formula (II):

where X has the same meaning as mentioned above and Hal represents halogen, with a glutamine-containing aqueous alkaline solution in the presence of a water-immiscible organic solvent; and recovering the N-(2-substituted)propionylglutamine compound from the reaction mixture.

DETAILED DESCRIPTION OF THE INVENTION

In the definition of the groups in formulae (I), (I') and (II), the alkyl moiety of the alkylsulfonyloxy includes, for example, a straight or branched alkyl having 1 to 6 carbon atoms, such as methyl, ethyl, propyl, isopropyl, butyl, isobutyl, sec-butyl, tert-butyl, pentyl and hexyl; the aryl moiety in the arylsulfonyloxy includes, for example, phenyl and naphthyl; and the substituted aryl includes, for example, tolyl. The halogen includes, for example, chlorine, bromine and iodine.

The water-immiscible organic solvent to be used in the process for producing an N-(2-substituted)propionylglutamine, includes, for example, ether, toluene, chloroform, methylene chloride, dichloroethane and ethyl acetate. The solvent may be used singly or as a mixture of them. Particularly, toluene, chloroform and methylene chloride are preferably used. The water-immiscible organic solvent is generally used in an amount of from 0.1 to 5 times-volumes, preferably from 0.3 to one time-volume, based on the amount of the glutamine-containing aqueous alkaline solution. The aqueous alkaline solution is not specifically restricted, so long as it does not interfere with the reaction. For instance, an aqueous solution of an inorganic alkaline substance such as sodium hydroxide, potassium hydroxide, lithium hydroxide, sodium carbonate or potassium carbonate and an aqueous solution of an organic alkaline substance such as trimethylamine, triethylamine or pyridine are mentioned. Preferably, sodium hydroxide, potassium hydroxide, sodium carbonate, potassium carbonate and triethylamine are used. Glutamine to be reacted is used in an amount of from 0.5 to 2.0 equivalents based on the 2-substituted-propionyl halide. One equivalent of glutamine is preferably used. Glutamine to be contained in the aqueous alkaline solution is used in an amount of from 0.01 to 3.0M, preferably from 0.1 to 1M. The reaction is carried out at a temperature of from $-5$ to $40°$ C., preferably from 0 to $10°$ C., in a period of from 0.1 to 5 hours, preferably from 0.5 to 2 hours. During the reaction, the pH value of the aqueous alkaline solution is kept from 7 to 11, preferably from 9 to 10.5. With the progress of the reaction, since hydrochloric acid is formed in the reaction mixture, the pH of the solution is lowered. Therefore, it is preferred to add a base to the reaction mixture during the reaction so as to adjust the pH of the reaction mixture to be within the above-mentioned range. The base to be used for the purpose is not specifically restricted, so long as it does not interfere with the reaction. For instance, inorganic bases such as sodium hydroxide and organic bases such as triethylamine are mentioned. Thus, Compound (I) is formed in a high yield in the aqueous alkaline solution.

The water-immiscible organic solvent is removed by liquid separation or the like. Then a salt is added to the resulting aqueous alkaline solution, and the pH of the solution is adjusted to be from 0.1 to 4, preferably from 0.5 to 2.5, with a strong acid such as hydrochloric acid or sulfuric acid, for salting-out of Compound (I) in a high yield. The salt to be used for the purpose includes, for example, sodium chloride, potassium chloride and sodium sulfate. Sodium chloride is preferably used. The amount of the salt to be added is not specifically restricted, and it is preferred that the aqueous alkaline solution may be a saturated solution of the salt.

Among from the N-(2-substituted)propionylglutamines to be obtained by the above-mentioned method, those represented by the formula (I'):

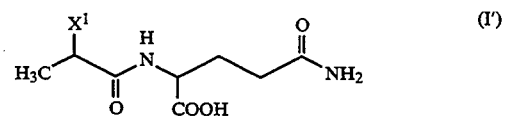

where $X^1$ represents chlorine, iodine, alkylsulfonyloxy, or substituted or unsubstituted arylsulfonyloxy, and a salt thereof are novel compounds. The salt of Compound (I') includes, for example, an alkali metal salt such as sodium or potassium salts, an ammonium salt such as ammonium, trimethylammonium or triethylammonium salts, and pyridinium salt.

Alanylglutamine is produced in a high yield, by reacting Compound (I) or its salt with ammonia.

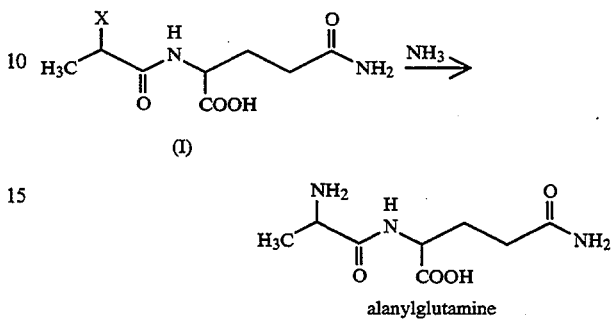

alanylglutamine

The reaction is usually carried out in a solvent. As the solvent to be used in the reaction, mention may be made of alcohols such as methanol, ethanol and propanol, as well as water and an aqueous solution of an alkaline substance such as sodium hydroxide or potassium hydroxide. Water is preferably used. Addition of an ammonium salt such as ammonium acetate, ammonium chloride, ammonium sulfate, ammonium bromide or ammonium carbonate to the reaction solution often elevates the reactivity. The reaction is generally carried out in the range of from $0°$ to $60°$ C. under atmospheric or compressed pressure. The reaction is completed in a period of from 1 to 100 hours, preferably from 4 to 50 hours. The ammonia may be used from 1 to 200 equivalents, preferably from 10 to 50 equivalents, based on Compound (I). The concentration of Compound (I) is from 0.01 to 2M, preferably from 0.1 to 0.6M. The progress of the reaction may be traced by high performance liquid chromatography (HPLC). After the completion of the reaction, the excess ammonia and water are removed from the reaction mixture, for example, by concentration under reduced pressure, and an alcohol, preferably methanol, ethanol or 2-propanol is added to the mixture to afford a highly purified alanylglutamine in a high yield. Where X is bromine in Compound (I), a highly purified alanylglutamine can be produced in a high yield, without racemization by carrying out the reaction at a temperature of $20°$ to $30°$ C.

Where an optical-active alanylglutamine is desired, an optical-active Compound (II) and an optical-active glutamine may be used. As the case may be, an optical-inactive Compound (II) and an optical-active glutamine may be used to obtain diastereomeric mixtures of Compound (I) or an alanylglutamine, which mixture may be separated and purified by an ordinary method.

The present invention will be explained in more detail by way of the following examples, which, however are not intended to restrict the scope of the present invention.

EXAMPLE 1

Production of N-(2-D-chloro)propionyl-L-glutamine 48.2 g (0.33 mol) of L-glutamine was added to 300 ml of water and 150 ml of toluene at room temperature and cooled to $0°$ to $5°$ C. 66 ml (0.33 mol) of 5N sodium hydroxide was added thereto to dissolve the L-glutamine therein. To the solution were added 90 ml of toluene containing 42.0 g (0.33 mol) of 2-D-chloropropionyl chloride having an optical purity of 92.8% ee and 74 ml of 5N sodium hydroxide, at 0° to 5° C. over a period of 2 hours, with maintaining the pH of the reaction solution to be 10. The mixture was stirred for one hour at 0° to 5° C., and toluene was removed by liquid separation. 60 g of sodium chloride was added to the aqueous layer at room temperature. To the solution was added 22 ml of concentrated hydrochloric acid at room temperature, and the pH of the mixture was adjusted to be 2.5. Then, crystal seeds were added to the mixture, and the mixture was stirred for 30 minutes. Further, 8 ml of concentrated hydrochloric acid was added thereto so that the pH was adjusted to be 1.0. The resulting solution was allowed to stand for one hour at room temperature. The crystals formed were taken out by filtration and dried under reduced pressure to obtain 71.6 g (yield: 85.3%, purity: 92.9%) of N-(2-D-chloro)propionyl-L-glutamine having an optical purity of 99.4% de and a melting point (with decomposition) of 148° C.

The physico-chemical properties of N-(2-D-chloro)propionyl-L-glutamine were as follows:

$^1$H-NMR (300 MHz, DMSO-$d_6$) δ (ppm): 1.54 (3H, d, J=6.6 Hz), 1.70~2.10 (2 H, m), 2.14 (2 H, t, J=7.1 Hz), 4.13~4.23 (1 H, m), 4.59 (1 H, q, J=6.7 Hz), 6.82 (1 H, s), 7.37 (1 H, s), 8.60 (1 H, d, J=7.7 Hz)

$^{13}$C-NMR (75.5 MHz, DMSO-$d_6$) δ (ppm): 21.7, 26.6, 31.2, 51.9, 54.1, 168.9, 172.8, 173.5

MS (CI, m/e): 237 (M$^+$+1)

IR (KBr, cm$^{-1}$): 1738, 1662

EXAMPLE 2

Production of N-[2-D-(p-toluenesulfonyloxy)]propionyl-L-glutamine 47.4g (0.32 mol) of L-glutamine was added to 300 ml of water and 150 ml of toluene at room temperature and cooled to 0° to 5° C. 66 ml (0.32 mol) of 5N sodium hydroxide was added thereto to dissolve the L-glutamine therein. To the solution were added 90 ml of toluene containing 91.0 g (0.32 mol) of 2-D-(p-toluenesulfonyloxy)propionyl chloride and 75 ml of 5N sodium hydroxide, at 0° to 5° C. over a period of 2 hours, with maintaining the pH of the reaction solution to be 10. The mixture was stirred for one hour at 0° to 5° C., and toluene was removed by liquid separation. 59 g of sodium chloride was added to the aqueous layer at room temperature. To the solution was added 25 ml of concentrated hydrochloric acid at room temperature, and the pH was adjusted to be 2.5. Then, crystal seeds were added to the solution, and the mixture was stirred for 30 minutes. Further, 8 ml of concentrated hydrochloric acid was added thereto so that the pH was adjusted to be 1.0. The resulting solution was allowed to stand for one hour at room temperature. The crystals formed were taken out by filtration and dried under reduced pressure to obtain 76.9 g (yield: 63.8%) of N-[2-D-(p-toluenesulfonyloxy)]propionyl-L-glutamine having an optical purity of 99.6% de and melting point of 102° C.

The physico-chemical properties of N-[2-D-(p-toluenesulfonyloxy)]propionyl-L-glutamine were as follows:

$^1$H-NMR (300 MHz, DMSO-$d_6$) δ (ppm): 1.35 (3 H, d, J=6.7 Hz), 1.72~1.98 (2 H, m), 2.03 (2 H, t, J=6.6 Hz), 2.43 (3 H, s), 4.07~4.14 (1 H, m), 4.90 (1 H, q, J=6.7 Hz), 6.83 (1 H, s), 7.31 (1 H, s), 7.48 (2 H, d, J=8.1 Hz), 7.82 (2 H, d, J=8.1 Hz), 8.44 (1 H, d, J=7.8 Hz)

$^{13}$C-NMR (75.5 MHz, DMSO-$d_6$-$D_2O$) δ (ppm): 19.8, 22.1, 27.4, 31.9, 52.3, 76.9, 128.6, 131.1, 133.4, 146.4, 169.4, 173.6, 175.2

MS (SIMS, m/e): 373 (M$^+$+1)

IR (KBr, cm$^{-1}$): 1712, 1675

EXAMPLE 3

Production of N-(2-D-methanesulfonyloxy)propionyl-L-glutamine 29.2g (0.20 mol) of L-glutamine was added to 185 ml of water and 92 ml of toluene at room temperature and cooled to 0° to 5° C. 40 ml (0.20 mol) of 5N sodium hydroxide was added thereto to dissolve the L-glutamine therein. To the solution were added 20 ml of toluene containing 38.0 g (0.20 mol) of 2-D-methanesulfonylpropionyl chloride and 50 ml of 5N sodium hydroxide, at 0° to 5° C. over a period of 2 hours, with maintaining the pH of the reaction solution to be 10. The mixture was stirred for one hour at 0° to 5° C., and toluene was removed by liquid separation. 76 g of sodium chloride was added to the aqueous layer at room temperature. To the solution was added 21 ml of concentrated hydrochloric acid at room temperature, and the pH was adjusted to be 0.9. The mixture was extracted twice with 150 ml of chloroform/2-propanol (1/1). The organic layer was taken out by separation and concentrated to dryness to obtain 27.2 g (yield: 45.8%) of N-(2-D-methanesulfonyloxy)propionyl-L-glutamine having an optical purity of 95.8% de.

The physico-chemical properties of N-(2-D-methanesulfonyloxy)propionyl-L-glutamine were as follows:

$^1$H-NMR (300 MHz, DMSO-$d_6$) δ (ppm): 1.47 (3 H, d, J=6.6 Hz), 1.77~2.12 (2 H, m), 2.15 (2 H, t, J=7.5 Hz), 3.23 (3 H, s), 4.17~4.24 (1 H, m), 5.07 (1 H, q, J=6.6 Hz), 6.84 (1 H, s), 7.35 (1 H, s), 8.60 (1 H, d, J=7.7 Hz)

$^{13}$C-NMR (75.5 MHz, DMSO-$d_6$) δ (ppm): 19.4, 25.6, 31.5, 51.9, 62.6, 75.9, 169.2, 173.2, 174.4

MS (SIMS, m/e): 297 (M$^+$+1)

EXAMPLE 4

Production of L-alanyl-L-glutamine from N-(2-D-chloro)propionyl-L-glutamine 60.0 g (0.24 mol) of N-(2-D-chloro)propionyl-L-glutamine having a purity of 92.9% and 600 ml of 28% aqueous ammonia were put into one-liter glass autoclave for dissolution at room temperature. The resulting solution was allowed to stand at 60° C. for 8 hours under the condition of an internal pressure of about 2 kg/cm$^2$. The reaction mixture was cooled to room temperature, and concentrated under reduced pressure, and 30 ml of water was added to the resulting residue to make 150 g as a whole. 450 ml of methanol was dropwise added to the resulting solution at room temperature over a period of one hour. The mixture was allowed to stand for 2 hours, and the crystals precipitated were taken out by filtration and dried under reduced pressure to obtain 35.4 g (yield: 69.0%) of a crude product of L-alanyl-L-glutamine having an optical purity of 97.6% de.

30 g of the crude product of L-alanyl-L-glutamine was dissolved in 50 ml of water, 0.6 g of active carbon was added thereto, and the mixture was stirred for 10 minutes at room temperature. The active carbon was removed by filtration, 42 ml of methanol was added to the filtrate at 30° C., and seed crystals were added thereto. Then, the mixture was allowed to stand for 2 hours. Further, 138 ml of methanol was added thereto at 30° C. over a period of one hour and then the mixture was stirred for 2 hours. The crystals precipitated were taken out by filtration and dried under reduced pressure to obtain 26.38 g (yield: 88%) of L-alanyl-L-glutamine having an optical purity of 99.9% de, a melting point (with decomposition) of 216° C., and a specific rotation $[\alpha]^{20}D$ of being $-3.49°$ (c=10, 1N-HCl).

EXAMPLE 5

Production of L-alanyl-L-glutamine from N-(2-D-bromo)propionyl-L-glutamine

In 300 ml of 28% aqueous ammonia, was dissolved 20.0 g (0.07 mol) of N-(2-D-bromo)propionyl-L-glutamine at room temperature and the solution was allowed to stand for 20 hours at room temperature. The reaction mixture was concentrated under reduced pressure, and about 6 ml of water was added to the resulting residue to make 40 g as a whole. 126 ml of methanol was dropwise added to the resulting solution at room temperature over a period of one hour, and the mixture was allowed to stand for 2 hours. The crystals thus formed were taken out by filtration and dried under reduced pressure to obtain 12.1 g (yield: 78.1%) Of a crude product of L-alanyl-L-glutamine having an optical purity of 98.9% de.

11.0 g of the crude product of L-alanyl-L-glutamine was dissolved in 18.3 ml of water, 0.22 g of active carbon was added thereto, and the mixture was stirred for 10 minutes at room temperature. The active carbon was removed by filtration, 15.4 ml of methanol was added to the resulting filtrate at 30° C., and seed crystals were added thereto. Then, the mixture was allowed to stand for 2 hours. Further, 50.6 ml of methanol was added thereto at 30° C. over a period of one hour, and the mixture was stirred for 2 hours. The crystals precipitated were taken out by filtration and dried under reduced pressure to obtain 9.84 g (yield: 89.5%) of L-alanyl-L-glutamine having an optical purity of 99.8% de.

EXAMPLE 6

Production of L-alanyl-L-glutamine from N-[2-D-(p-toluenesulfonyloxy)]propionyl-L-glutamine In 300 ml of 28% aqueous ammonia, was dissolved 30.0 g (0.08 mol) of N-[2-D-(p-toluenesulfonyloxy)]propionyl-L-glutamine at room temperature, and the solution was allowed to stand for 24 hours at room temperature. The reaction mixture was concentrated under reduced pressure, and about one ml of water was added to the resulting residue to make 50 g as a whole. 200 ml of methanol was dropwise added to the resulting solution at room temperature over a period of one hour, and the mixture was allowed to stand for 2 hours. The crystals thus formed were taken out by filtration and dried under reduced pressure to obtain 8.6 g (yield: 49.1%) of a crude product of L-alanyl-L-glutamine having an optical purity of 99.3% de.

8 g of the crude product of L-alanyl-L-glutamine was dissolved in 13.3 ml of water, 0.16 g of active carbon was added thereto, and the mixture was stirred for 10 minutes at room temperature. The active carbon was removed by filtration, 11.2 ml of methanol was added to the resulting filtrate at 30° C., and seed crystals were added thereto. Then, the mixture was allowed to stand for 2 hours. Further, 36.8 ml of methanol was added thereto at 30° C. over a period of one hour and then the mixture was stirred for 2 hours. The crystals precipitated were taken out by filtration and dried under reduced pressure to obtain 7.41 g (yield: 92.6%) of L-alanyl-L-glutamine having an optical purity of 99.9% de.

EXAMPLE 7

Production of L-alanyl-L-glutamine from N-(2-D-methanesulfonyloxy)propionyl-L-glutamine In 156 ml of 28% aqueous ammonia, was dissolved 15.6 g (0.053 mol) of N-(2-D-methanesulfonyloxy)propionyl-L-glutamine at room temperature, and the solution was allowed to stand for 46 hours. The reaction mixture was concentrated under reduced pressure, and about 7 ml of water was added to the resulting residue to make 35 g as a whole. 100 ml of methanol was dropwise added at room temperature over a period of one hour and the mixture was allowed to stand for 2 hours. The crystals thus formed were taken out by filtration and dried under reduced pressure to obtain 5.78 g (yield: 50.5%) of a crude product of L-ananyl-L-glutamine having an optical purity of 96.4% de.

5.0 g of the crude product of L-alanyl-L-glutamine was dissolved in 8.3 ml of water, 0.1 g of active carbon was added thereto, and the mixture was stirred for 10 minutes at room temperature. The active carbon was removed by filtration, 7.0 ml of methanol was added to the resulting filtrate at 30° C., and seed crystals were added thereto. Then, the mixture was allowed to stand for 2 hours. Further, 23.0 ml of methanol was added thereto at 30° C. over a period of one hour and then the mixture was stirred for 2 hours. The crystals precipitated were taken out by filtration and dried under reduced pressure to obtain 4.30 g (yield: 86.0%) of L-alanyl-L-glutamine having an optical purity of 99.0% de.

EXAMPLE 8

Amination of N-(2-D-bromo)propionyl-L-glutamine

In 3 ml of 28% aqueous ammonia, was dissolved 300 mg (1.07 mmol) of N-(2-D-bromo)propionyl-L-glutamine having an optical purity of 97.9% de at room temperature, and the solution was allowed to stand for 20 hours at room temperature, in the same manner as in Example 5. The reaction mixture was concentrated under reduced pressure and ammonia was removed therefrom by evaporation. By HPLC analysis under the following condition, formation of 202 mg (yield: 87.1%) of L-alanyl-L-glutamine having an optical purity of 98.2% de was confirmed.

Condition for HPLC Analysis:
Column: YMC-pack, ODS-AQ313
Mobile Phase: 0.01M $KH_2PO_4$
Detection: UV 210 nm Separately, N-(2-D-bromo)propionyl-L-glutamine was aminated according to the method described in Hoppe-Seyler's Z. Physiol. Chem., 105, 58 (1919):

In 2 ml of 26.7% aqueous ammonia, was dissolved 300 mg (1.07 mmol) of N-(2-D-bromo)propionyl-L-glutamine having an optical purity of 97.9% de at room temperature. The solution was allowed to stand for one hour in water bath of 100° C. The reaction mixture was concentrated under reduced pressure and ammonia was removed therefrom by evaporation. By HPLC analysis under the same condition as mentioned above, formation of 147 mg (yield: 63.4%) of L-alanyl-L-glutamine having an optical purity of 96.8% de was confirmed.

EXAMPLE 9

Production of N-(2-D-bromo)propionyl-L-glutamine 21.9 g (0.15 mol) of L-glutamine was added to 300 ml of water and 75 ml of toluene at room temperature, and the mixture was cooled to 0° to 5° C. 30 ml (0.15 mol) of 5N sodium hydroxide was added thereto to dissolve L-glutamine therein. 30 ml of toluene containing 25.7 g (0.15 mol) of 2-D-bromopropionyl chloride was added to the resulting solution at 0° to 5° C. over a period of 2 hours, while maintaining the pH of the reaction solution to be 10 by dropwise adding 25 ml of 5N sodium hydroxide thereto. The mixture was stirred for one hour at 0° to 5° C., toluene was removed by liquid separation, and 40 g of sodium chloride was added to the aqueous layer at room temperature.

15 ml of concentrated hydrochloric acid was added to the resulting solution at room temperature so as to adjust the pH to be 1.0, and the solution was allowed to stand for one hour at room temperature. The crystals formed were taken out by filtration and dried under reduced pressure to obtain 40.4 g (yield: 95.8%) of N-(2-D-bromo)propionyl-L-glutamine having an optical purity of 97.9% de and a melting point of 142° C.

What is claimed is:

1. A process for producing alanylglutamine, which comprises reacting an N-(2-substituted)-propionylglutamine compound represented by the formula (I):

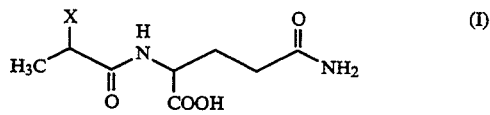

where X represents halogen, alkylsulfonyloxy, or substituted or unsubstituted arylsulfonyloxy, with ammonia in a reaction mixture at a temperature of 60° C. or below; and recovering alanylglutamine from the reaction mixture.

2. A process for producing L-alanyl-L-glutamine, which comprises reacting N-(2-D-bromo)-propionyl-L-glutamine with ammonia in a reaction mixture at room temperature and recovering L-alanyl-L-glutamine from the reaction mixture.

* * * * *

UNITED STATES PATENT AND TRADEMARK OFFICE
CERTIFICATE OF CORRECTION

PATENT NO. : 5,380,934

DATED : January 10, 1995

INVENTORS : Kunimi Inoue et al.

It is certified that error appears in the above-identified patent and that said Letters Patent is hereby corrected as shown below:

ON TITLE PAGE

In [54] TITLE, "ALANYLGUTAMINE" should read
--ALANYLGLUTAMINE--.
In [56] FOREIGN PATENT DOCUMENTS, "Germany" should read
--Federal Republic of Germany--.
In [56] OTHER PUBLICATIONS, "Sturcutre"," should read
--Structure",--.

COLUMN 1

Line 2, "ALANYLGUTAMINE" should read --ALANYLGLUTAMINE--.
Line 6, "N-(2substituted)" should read
--N-(2-substituted)--.
Line 9, "N-(2substituted)-" should read
--N-(2-substituted)---.
Line 18, "comprising" should read --comprises--.
Line 25, "comprising" should read --comprises--.
Line 30, "reacting" should read --reacts--.

UNITED STATES PATENT AND TRADEMARK OFFICE
CERTIFICATE OF CORRECTION

PATENT NO. : 5,380,934

DATED : January 10, 1995

INVENTORS : Kunimi Inoue et al.

It is certified that error appears in the above-identified patent and that said Letters Patent is hereby corrected as shown below:

COLUMN 2

Line 5, "comprising" should read --comprises--.

Signed and Sealed this

Sixth Day of June, 1995

Attest:

BRUCE LEHMAN

Attesting Officer

Commissioner of Patents and Trademarks